(12) United States Patent
de la Fuente

(10) Patent No.: US 6,170,678 B1
(45) Date of Patent: Jan. 9, 2001

(54) MODULAR DISPLAY FOR CONSUMER PRODUCTS

(75) Inventor: Ramon de la Fuente, Col. San angel Tetelpan (MX)

(73) Assignee: Recot, Inc., Pleasanton, CA (US)

( * ) Notice: Under 35 U.S.C. 154(b), the term of this patent shall be extended for 0 days.

(21) Appl. No.: 09/131,664

(22) Filed: Aug. 10, 1998

(30) Foreign Application Priority Data

Aug. 15, 1997 (MX) .................................................. 976269

(51) Int. Cl.[7] .............................. A47F 1/12; A47B 57/04; A47B 57/58
(52) U.S. Cl. ...................... 211/59.2; 211/184; 211/187; 248/242
(58) Field of Search .................................. 211/59.2, 184, 211/187, 40; 248/242, 243; 220/4.28, 4.32, 485, 489, 527, 529, 532, 633, 634, 635

(56) References Cited

U.S. PATENT DOCUMENTS

| | | |
|---|---|---|
| D. 139,534 | 11/1944 | Adams . |
| 996,636 | 7/1911 | Gabriel . |
| 1,700,212 | 1/1929 | Arlt . |
| 1,760,854 | 5/1930 | Wright . |
| 1,961,394 | 6/1934 | Rothe . |
| 2,319,589 | 5/1943 | Drinkwater . |
| 2,572,780 | 10/1951 | Tackenberg . |
| 3,272,528 | 9/1966 | Young et al. . |
| 3,628,807 | 12/1971 | Ballwin et al. . |
| 3,797,842 | 3/1974 | Swick, Jr. et al. . |
| 3,861,702 | 1/1975 | Wilson . |
| 3,891,228 | 6/1975 | Rhinehart et al. . |
| 4,067,265 | 1/1978 | Watson . |
| 4,094,526 | 6/1978 | Clarke et al. . |
| 4,679,805 | 7/1987 | Cunningham . |
| 4,793,497 | 12/1988 | Hall et al. . |
| 4,901,872 | 2/1990 | Lang . |
| 5,040,690 | 8/1991 | van der Schoot . |
| 5,718,441 | 2/1998 | Kern et al. . |

Primary Examiner—Daniel P. Stodola
Assistant Examiner—Erica B Harris
(74) Attorney, Agent, or Firm—Rothwell, Figg, Ernst & Manbeck

(57) ABSTRACT

A modular display for consumer products, contains a support frame, several modular display shelves that can be displaced in a rotating manner upwards and downwards in relation to the frame, several containment elements that can slide laterally on a support grille, frontal securing elements and bracket elements that allow the modular shelves to rotate. The modular display allows the products to stay organized, contained and permanently at the front of the display. The display also facilitates the counting and distribution of the products. In addition, the modular display allows products of different dimensions, to be displayed, by simple adjustments to their configuration.

17 Claims, 10 Drawing Sheets

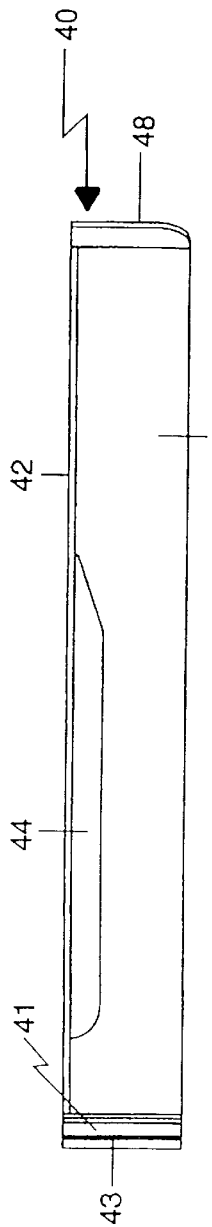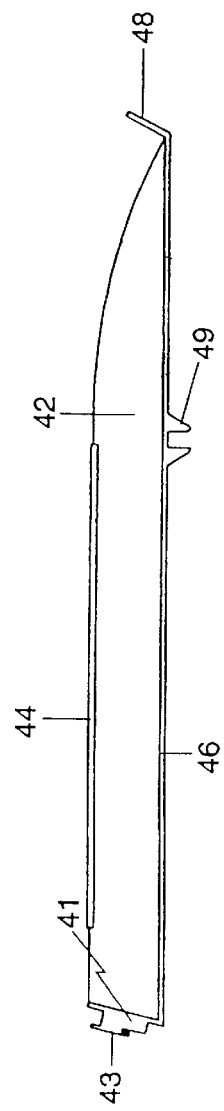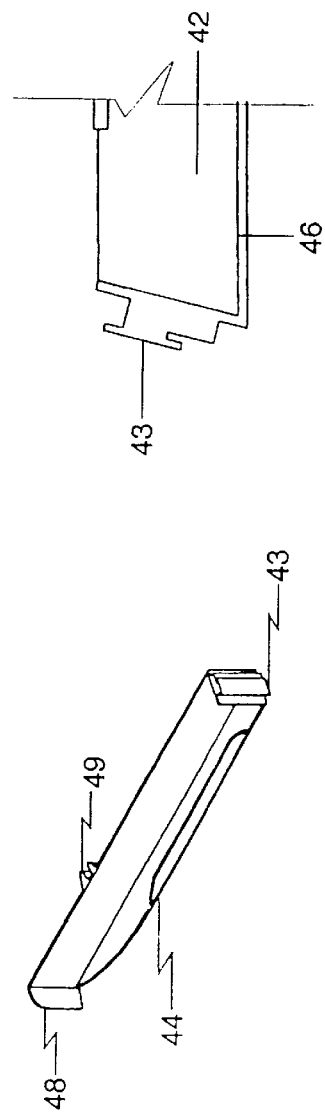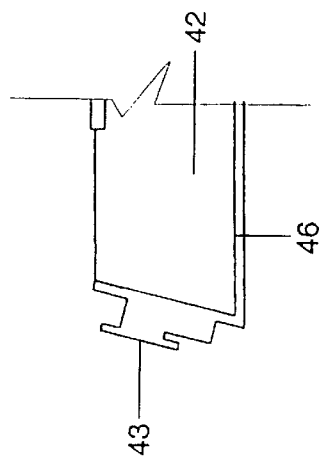
FIG. 4A
FIG. 4B
FIG. 4C
FIG. 4D

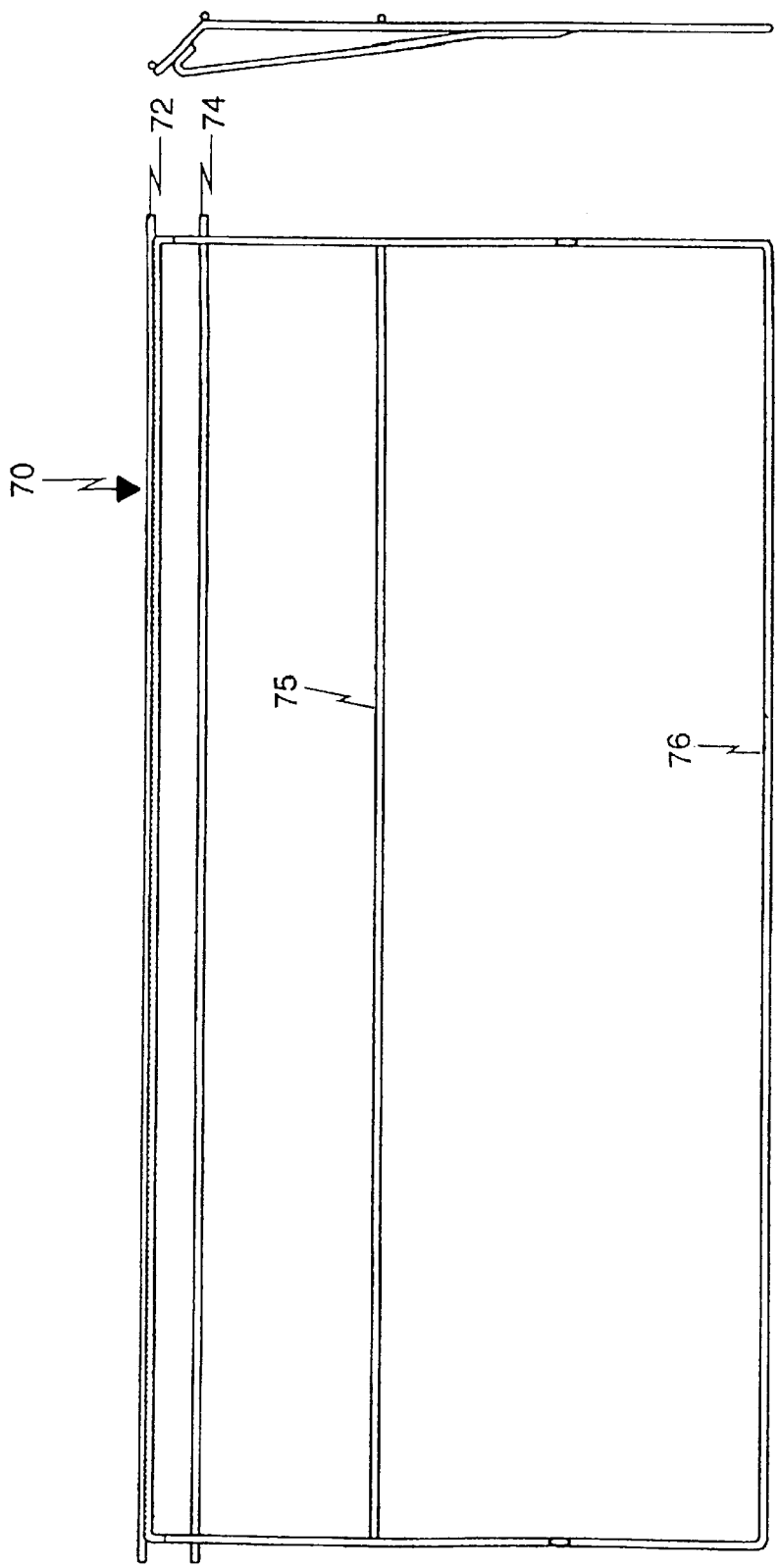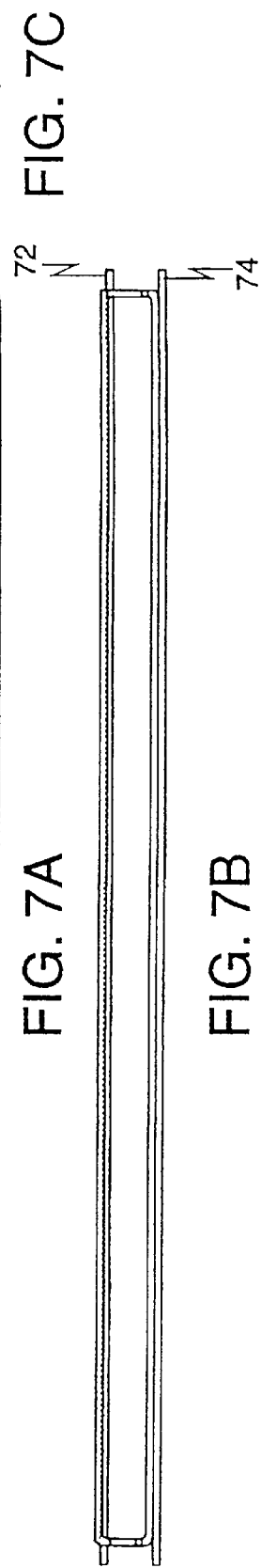
FIG. 7A
FIG. 7B
FIG. 7C

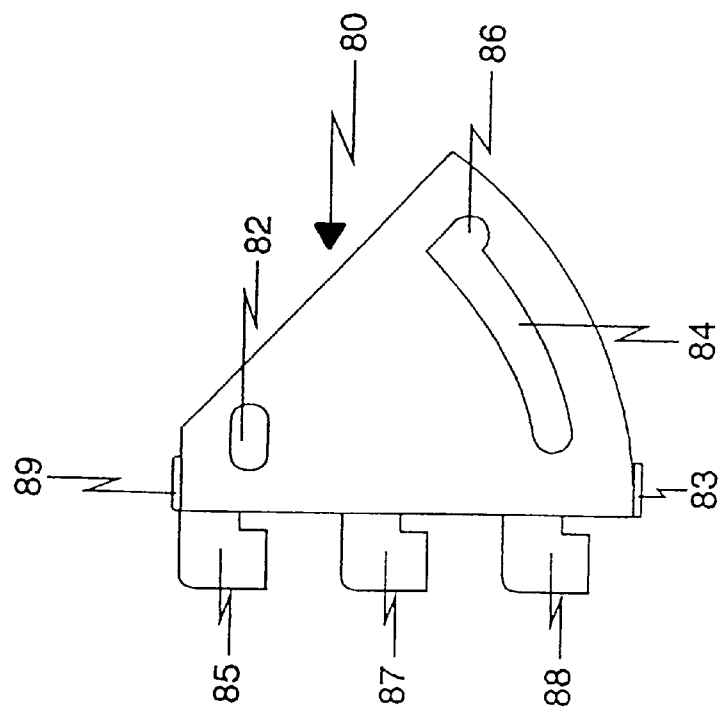
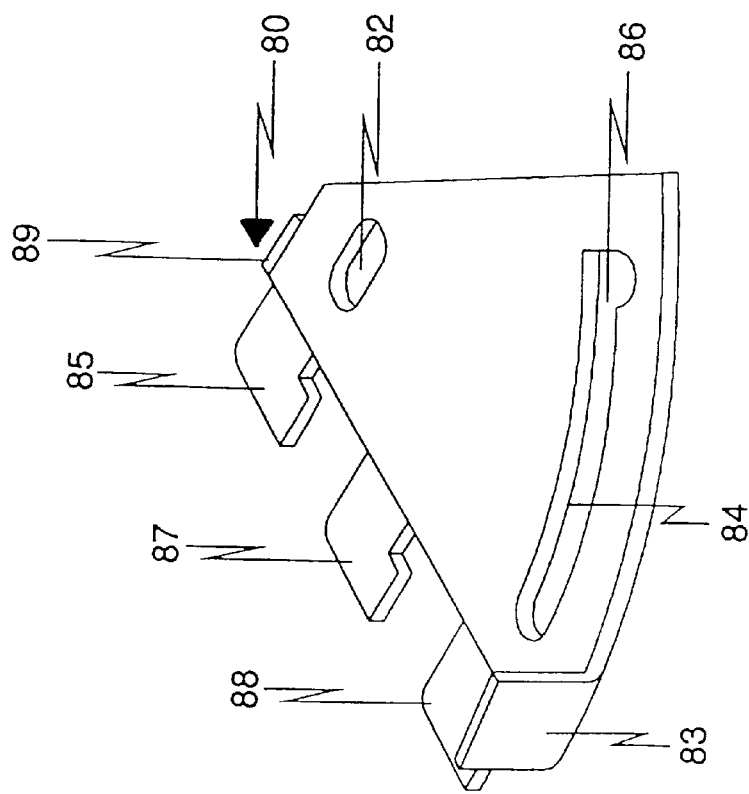
FIG. 8B
FIG. 8A

MODULAR DISPLAY FOR CONSUMER PRODUCTS

BACKGROUND OF THE INVENTION

One of the most important aspects of the industry of manufacturing and distributing consumer products such as snacks, fried foods, bread, cookies, sweets and similar items, is the way in which the products are displayed to the consumer at points of sale.

Consumer products should be displayed in such a way that they are always within the consumer's reach, well ordered and classified in the display; in addition, the display must facilitate the substitution and replacement of such products by distribution personnel.

Market studies have demonstrated that the sales of a product increase significantly when the product is permanently "put forward," i.e., whenever the products are placed at the front of the display, so as to catch the attention of the consumer and allow for easy removal from the display.

On the other hand, the consistency, weight and geometry of products packed in plastic bags, for example snacks, make it particularly difficult for the displayed products to remain well ordered, and to be pushed towards the front of the display.

Several types of displays are known for consumer products, generally consisting of a series of shelves and panels with divisions in order to accommodate in rows the various products to be exhibited for sale. However, these displays do not keep the product up front and are difficult for the distributors to replenish.

Another known type of display is that which is described in Mexican patent application No. 9603837, which has the advantage of maintaining the products in order and permanently at the front of the display, while also facilitating their filling by the distributors. However, in spite of its advantages, said display has a relatively complicated structure, in which all the shelves of the display are displaced upwards and downwards together, and the products are placed on trays with pre-established sizes, which limit the placement of products of different sizes on the display. On the other hand, due to the structural characteristics of this display, it is certainly difficult to quickly assemble and disassemble it, which makes its transport and distribution to points of sale difficult.

In view of the above, one of the objectives of this invention is to supply a product display which keeps the products orderly and permanently at the front of the display, in spite of their gradual removal from the display.

Another objective of this invention is to supply a versatile consumer product display, allowing the display of products of various sizes, height and width, with simple adjustments in its configuration.

Another objective of the invention is to supply a display that facilitates the distribution, counting, and accommodation of the products at the point of sale.

Yet another objective of this invention is to supply a modular display, with a simple structure and construction, facilitating its transport and assembly at the point of sale.

These and other objectives of the invention will become apparent from the description of the preferred embodiment detailed below.

BRIEF DESCRIPTION OF THE INVENTION

This invention concerns a modular product display which includes:

a support frame 90;

several modular display shelves 11, 13, 15, 17 and 19, which can be displaced by revolving them upwards and downwards in relation to the back of the support frame 90;

in which the structural elements 94 of said frame 90 include at least one longitudinal row of grooves 95 suitable to receive said display shelves in various positions, depending on the height of the product to be displayed;

each of said modular display shelves includes a support grille 70, two elements for containment at the ends 40, several intermediary containment elements 50 of the products to be displayed, which may be slid laterally on the support grille 70 in order to adjust to the width of the products to be displayed, frontal securing elements 60 to secure the containment elements, and bracket elements 80 which join said display shelves 11, 13, 15, 17 and 19, to said frame 90, and allow the front end of said display shelves to rotate upwards and downwards in relation to the frame, and to maintain the display shelf in an inclined lower position, or in a horizontal upper position;

as such, the modular display allows products of various sizes to be displayed, with the product sliding through the containment elements towards the front of the display, as the consumers remove the products contained therein.

BRIEF DESCRIPTION OF THE DRAWINGS

FIG. 4A is a plane view from above of one of the lateral containment elements in FIG. 3, while the other end is a mirror image of same;

FIG. 4B is an elevated lateral view of the lateral containment elements in FIG. 4A;

FIG. 4C is a frontal perspective of the lateral containment elements in FIG. 4A;

FIG. 4D is an elevated detailed lateral view of the frontal part of the lateral containment elements in FIG. 4B;

FIG. 7A is a plane view from above of the support grille in FIG. 7;

FIG. 7B is a frontal elevated view of the support grille in FIG. 7;

FIG. 7C is a lateral elevated view of the support grille in FIG. 7;

FIG. 8A is a view of the bracket elements in FIG. 3;

FIG. 8B is a frontal elevated view of the bracket elements in FIG. 8A;

DESCRIPTION OF THE PREFERRED EMBODIMENTS

Figure 1:
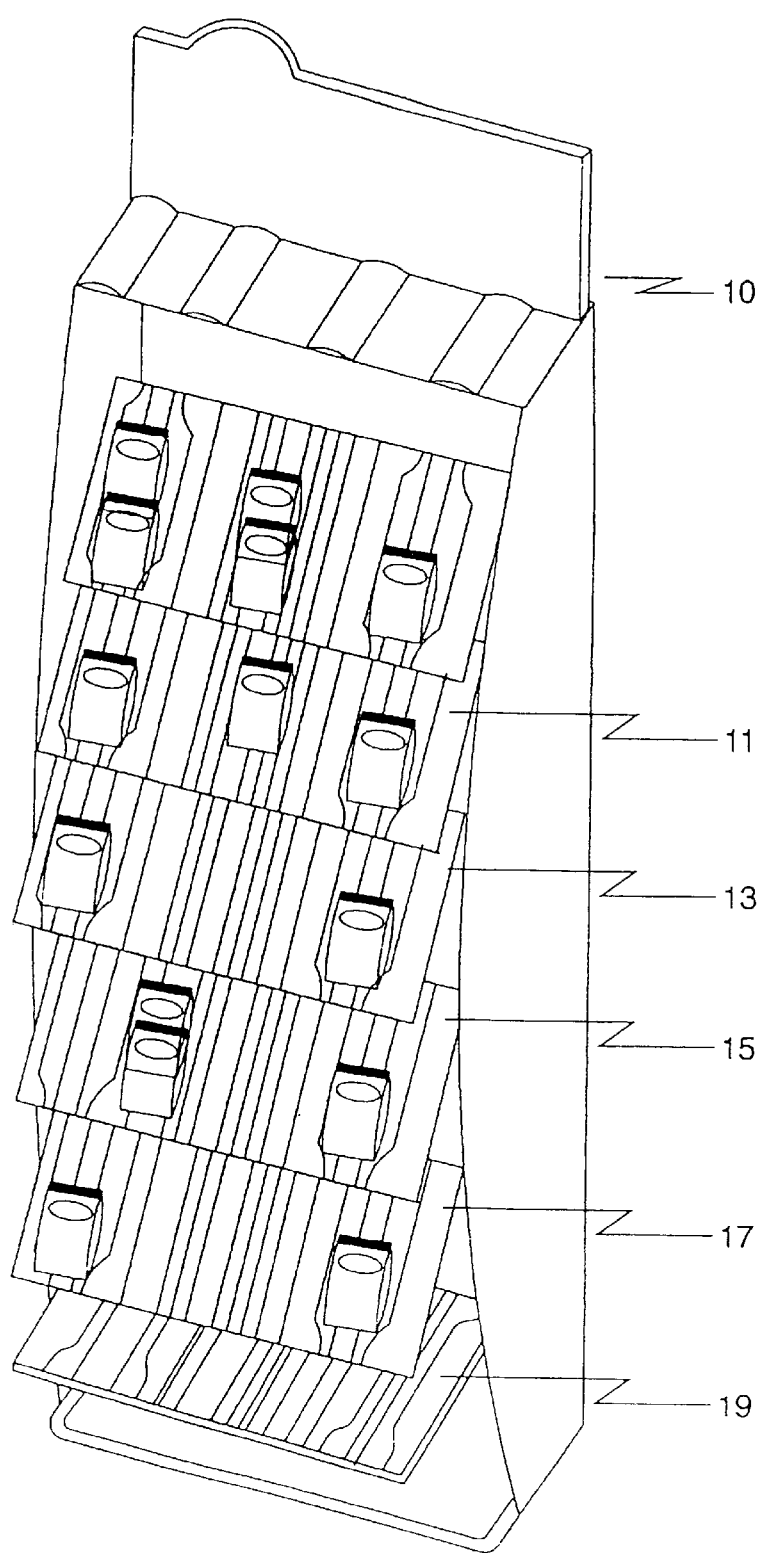
FIG. 1 is a schematic perspective of an embodiment of the modular product display under this invention, showing the shelves in their inclined position.
Figure 2:
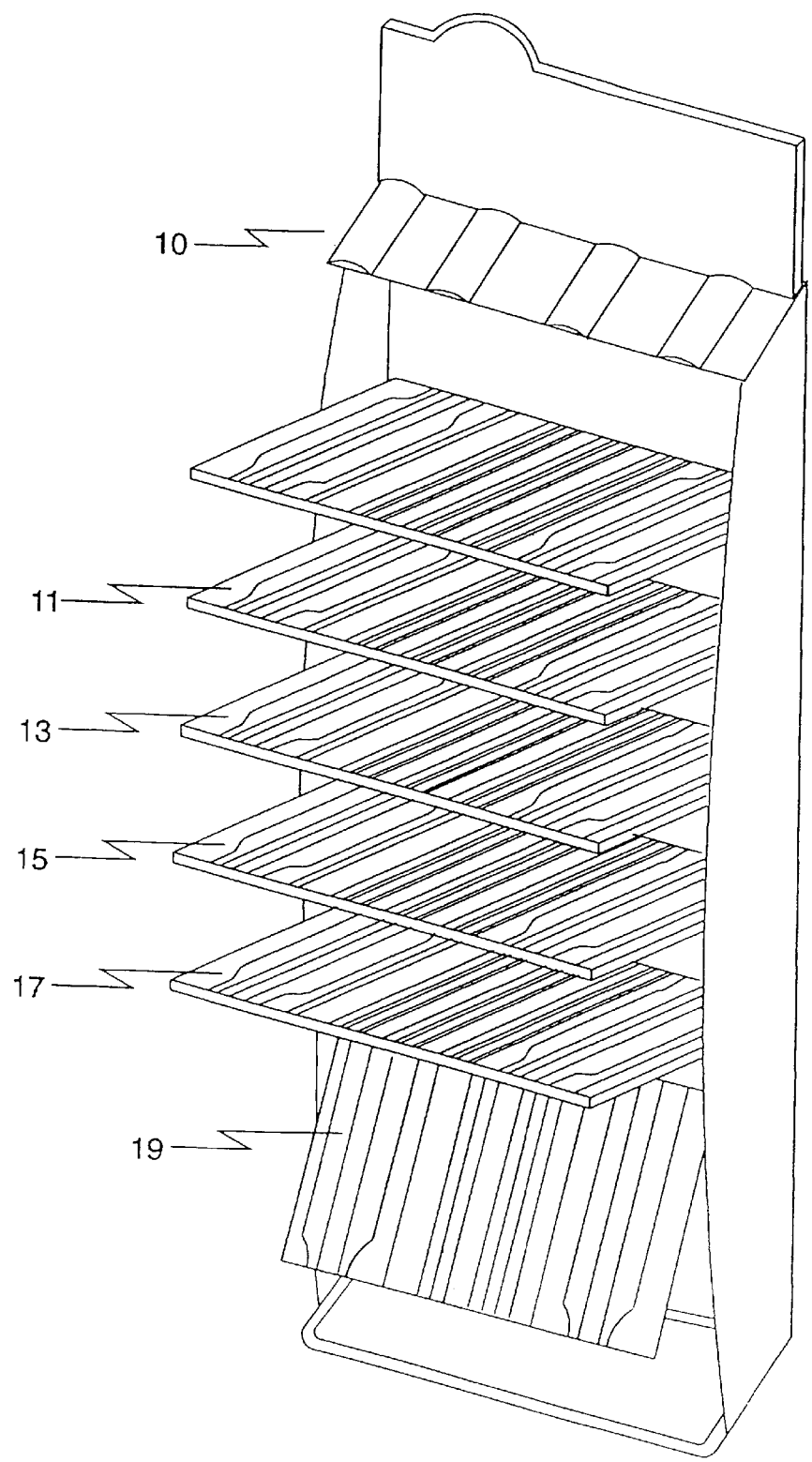
FIG. 2 is a schematic perspective, similar to FIG. 1, showing one of the shelves in its horizontal position.

FIGS. 1 and 2 illustrate in a general schematic manner this invention's modular product display 10, which includes a frame 90 (see FIGS. 9A to 9C), several decorative elements 12, 14, 16, 26 and 27 (see FIG. 3), joined to frame 90 and several display shelves 11, 13, 15, 17 and 19, which can be displaced upwards and downwards rotating in relation to the frame 90.

FIG. 1 shows display shelves 11, 13, 15, 17 and 19, in their downward position, the position in which they remain in order to display the products contained therein.

FIG. 2 shows display shelves 11, 13, 15 and 17 in their horizontal position, the position in which the shelves are placed by distribution personnel in order to replenish them and change products, while display shelf 19 remains in its downward position.

Figure 3:
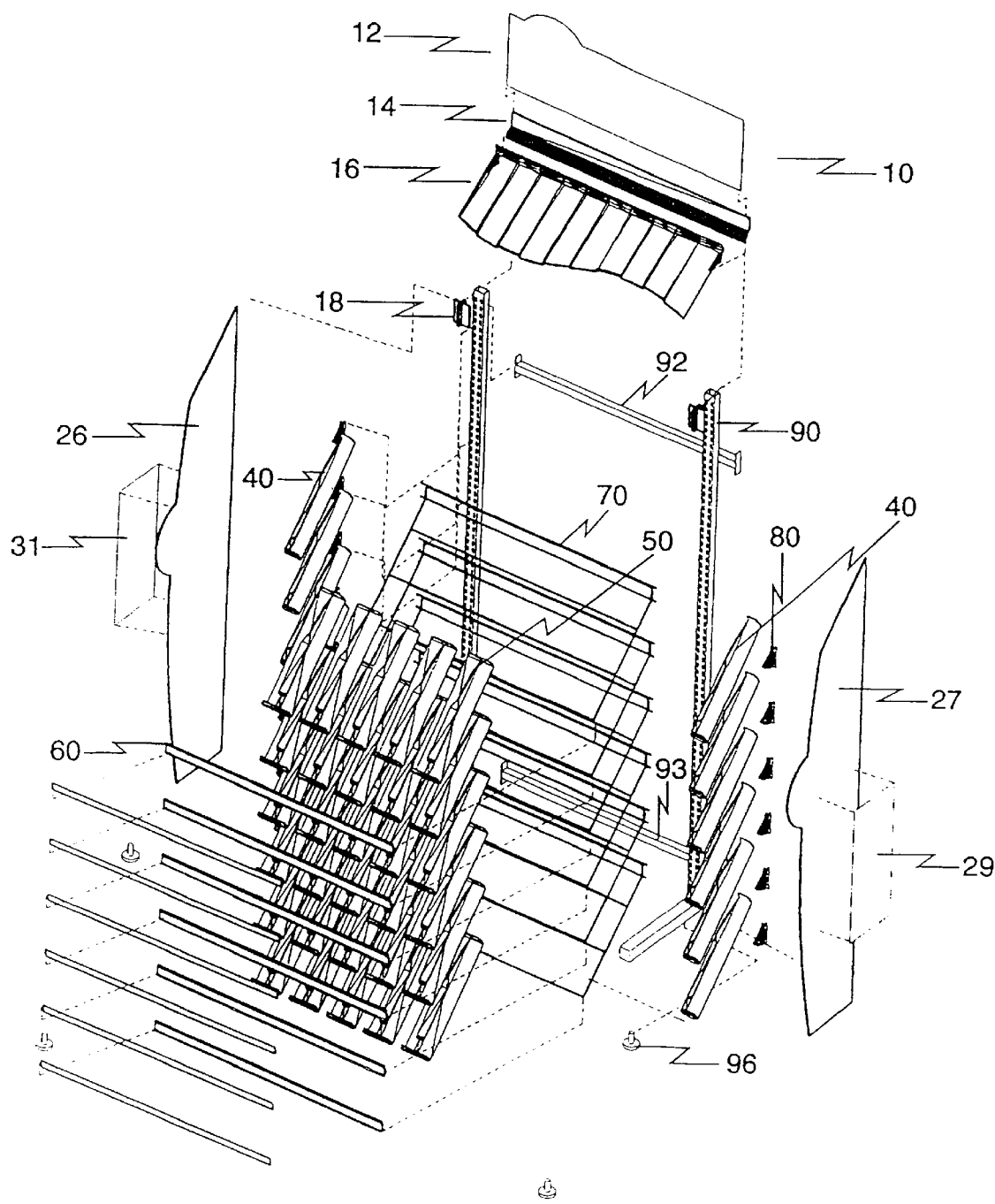
FIG. 3 is a detailed view of the modular display in FIG. 1.

FIG. 3 shows a detailed view of the various elements composing the invention's modular display. The invention will now be described with reference to FIG. 3 and the following Figures, which illustrate each of the elements of the modular display in more detail.

Each of the display shelves is joined to a frame 90, with a variable number of display shelves, whereby the separation between them depends on the size of the products to be displayed in each of them, i.e., the modular display allows products of different sizes to be displayed, depending on specific display needs.

Figure 9C:
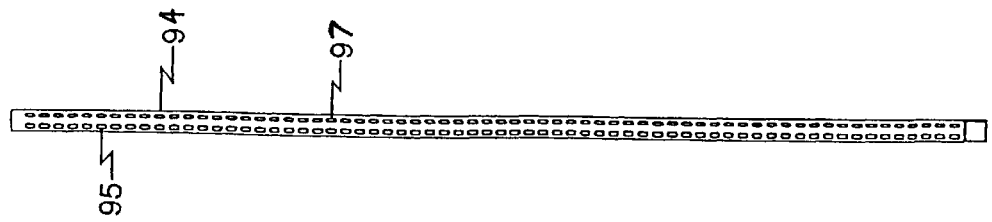
FIG. 9C is an elevated frontal view of one of the stringers in the frame elements in FIG. 9A.
Figure 9B:
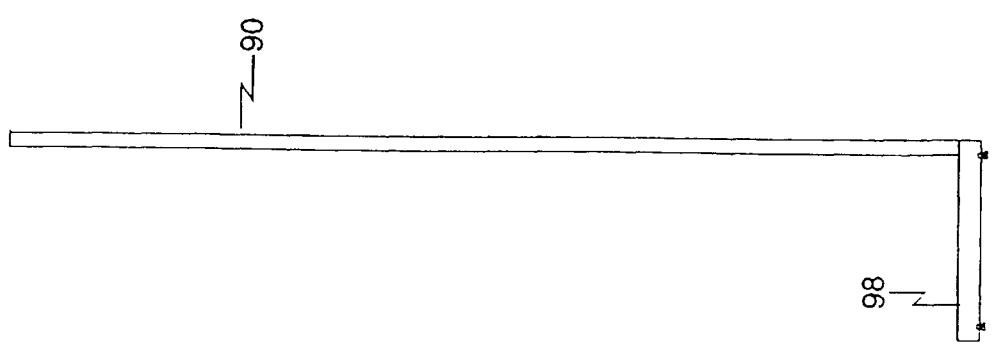
FIG. 9B is an elevated lateral view of the frame elements in FIG. 9A.
Figure 9A:
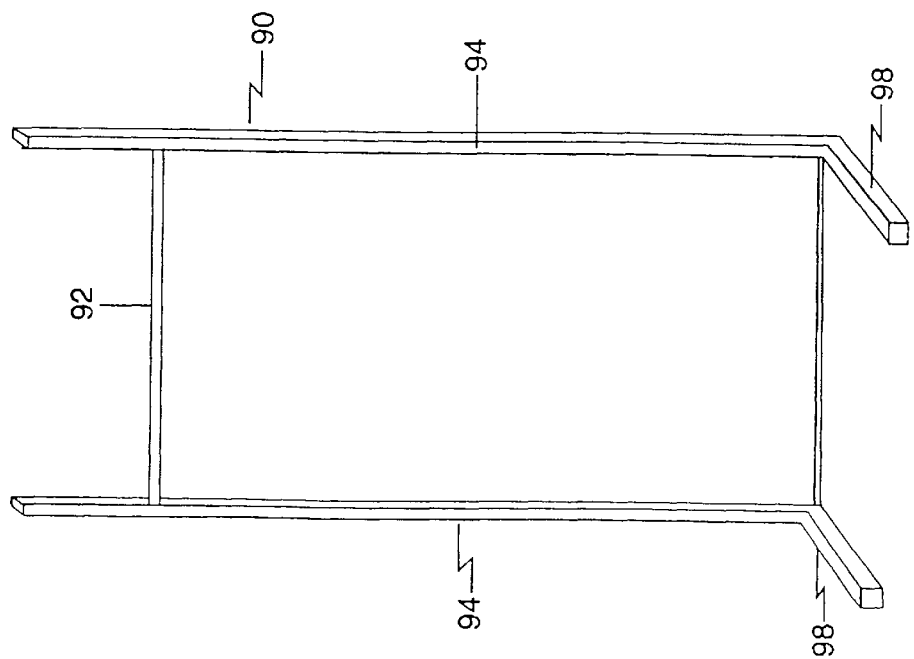
FIG. 9A is a view of the frame elements in FIG. 3.

As shown in FIGS. 9A to 9C, the frame 90 consists of two stringers 94, joined in their lower part to the base elements 98, which, together with the stringers 94, have an L-shape configuration, as can be seen in FIG. 9B. The two L-shaped elements are joined by two reinforcement crosspieces 92 and 93 (see FIG. 3), placed crosswise between them. In addition to giving structural resistance to the frame, these crosspieces 92 and 93 establish the distance that must exist between the two stringers 94.

The stringers 94 include two parallel longitudinal rows of grooves 95 and 97, receiving the brackets which support each of the various modular display shelves 11, 13, 15, 17 and 19 in a fixed position, depending on the desired separation between each of said shelves, as will be described in more detail below.

In FIG. 3, each of the display shelves includes two sliding end containment elements 40, several sliding intermediary containment elements 50, a support grille 70, two brackets 80 and frontal securing elements 60.

In the preferred embodiment, each of the display shelves includes two sliding end containment elements 40, and five or more sliding intermediary containment elements 50. However, this configuration may vary depending on display needs.

As can be seen from FIGS. 4A to 4D, each of the end containment elements 40 consists of a frontal wall 41, a lateral wall 42, a back wall 48 and a bottom wall 46. The outside of the frontal wall 41 has a securing profile 43, and the outside of the bottom wall has a securing U-shaped projection 49. On the upper part of the wall 42 there is a guide element 44 which, as described below, helps keep the products organized.

Figure 5A:
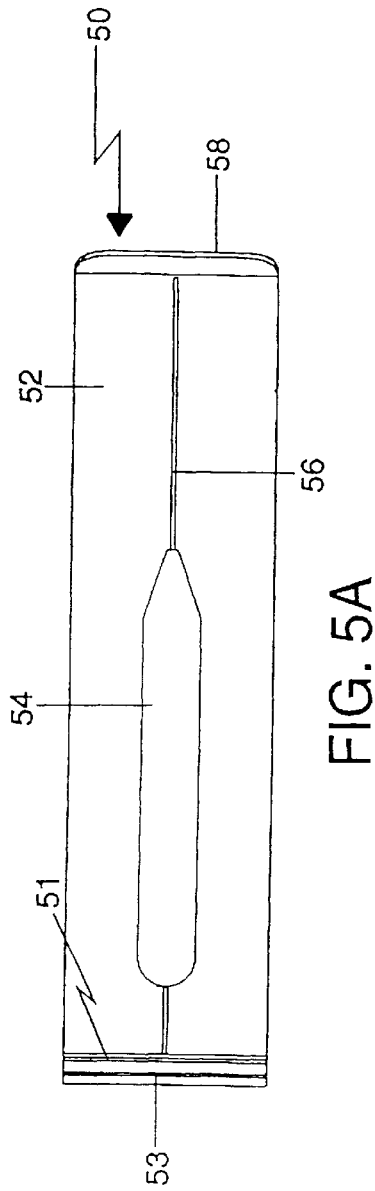
FIG. 5A is a plane view from above of one of the intermediary containment elements in FIG. 3.
Figure 5B:
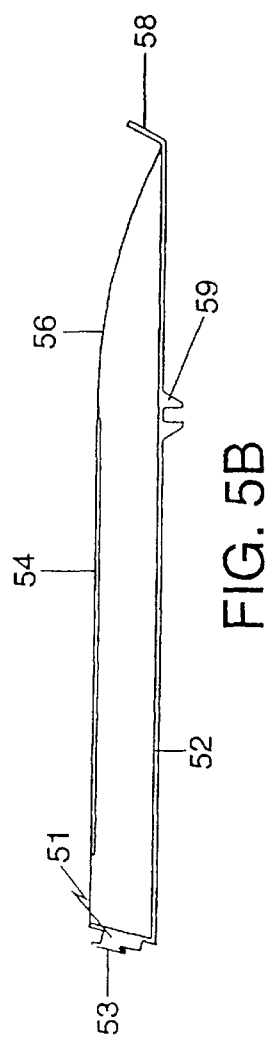
FIG. 5B is an elevated lateral view of the intermediary containment elements in FIG. 5A.
Figure 5C:
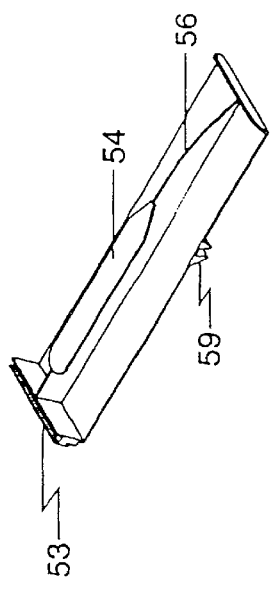
FIG. 5C is a posterior view of the intermediary containment elements in FIG. 3A.

On the other hand, as can be seen in FIGS. 5A to 5C, each of the intermediary containment elements has a frontal wall 51, a central wall 56, a back wall 58 and a bottom wall 52. The outside of frontal wall 51 has a securing profile 53, and the outside of the bottom wall has a securing U-shaped projection 59. On the upper part of intermediary wall 56 there is a guide element 54 that acts in conjunction with guide element 44 of the sliding end containment elements 40 to help keep the products organized.

Figure 7:
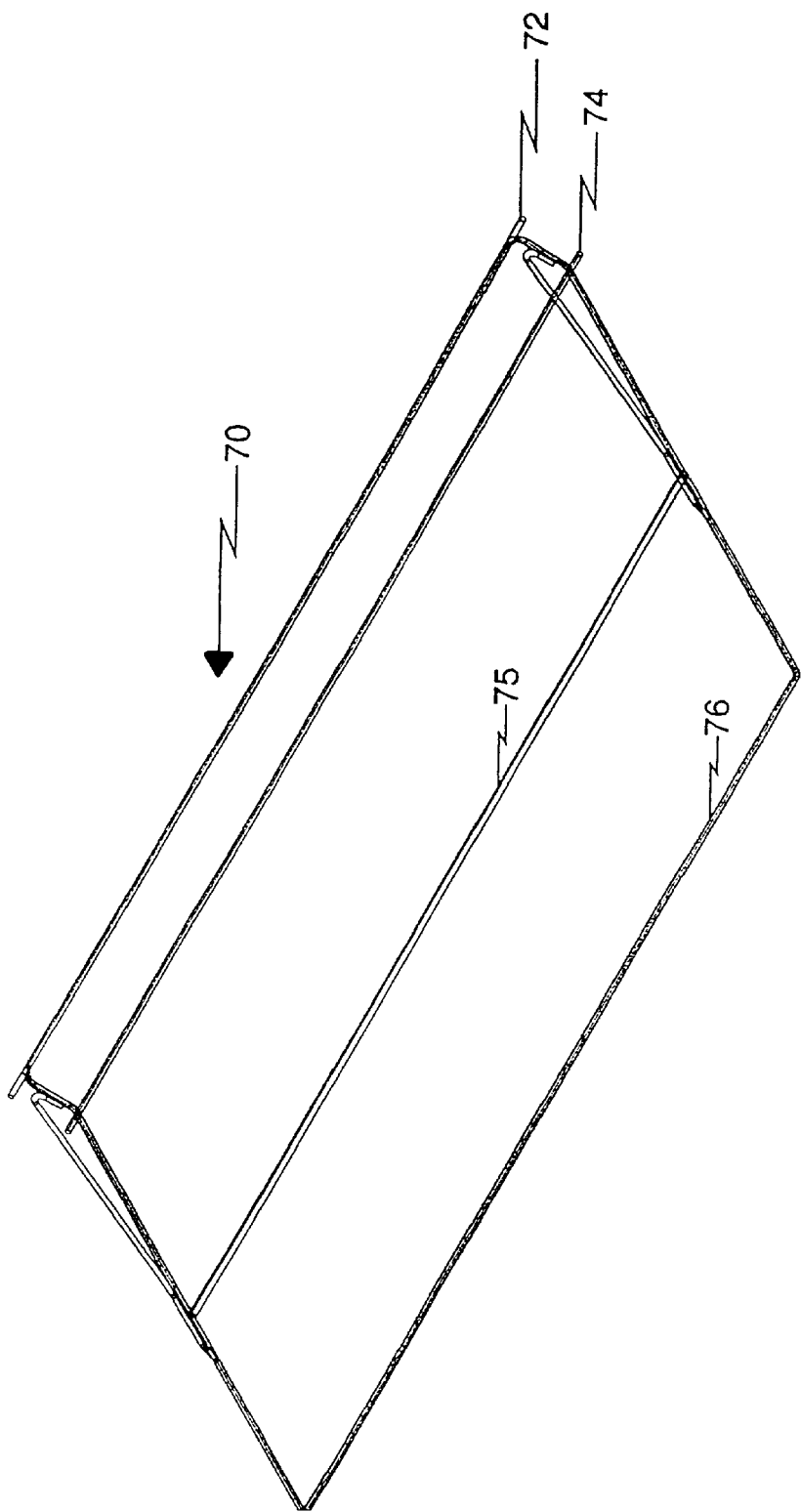
FIG. 7 is a perspective of the support grille in FIG. 3.

End and intermediary containment elements are joined to the grille 70, inserting the rod 75, see FIG. 7, into the U-shaped elements 49 and 59, respectively, of the sliding end and intermediary elements 40 and 50, so that the containment elements remain fixed in said grille 70, and can be slid laterally, so that the channel formed between walls 42 and 56 and the channel or guide formed by elements 44 and 54 can be adjusted to the size of the product displayed, and the product may be slid towards the front of the display when the display shelf is placed in its inclined position.

Figure 6A:
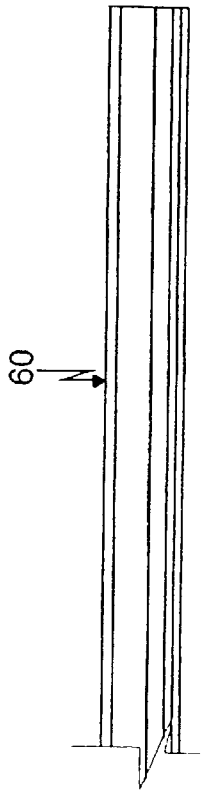
FIG. 6A is an elevated posterior view of the frontal containment elements in FIG. 3.
Figure 6C:
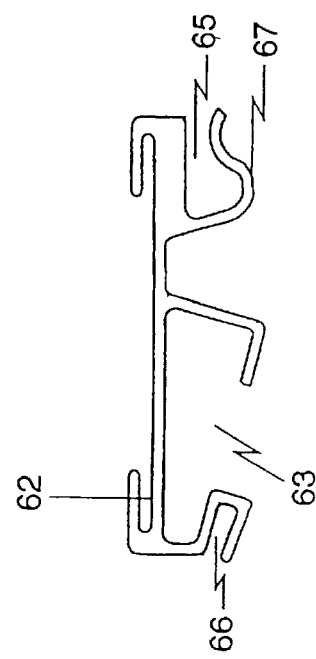
FIG. 6C is an additional cross section view of the frontal containment elements in FIG. 6A.
Figure 6B:
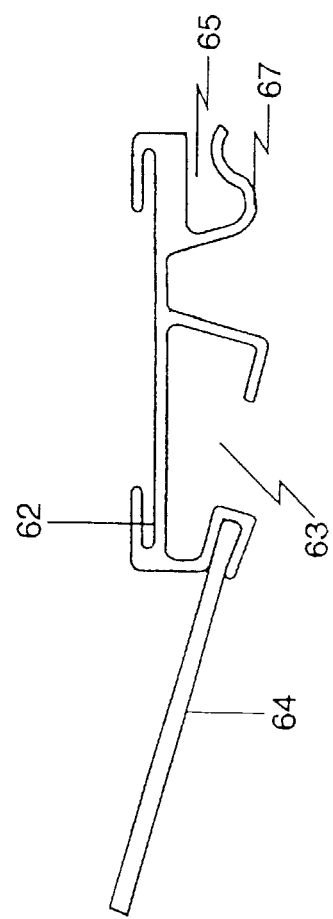
FIG. 6B is a cross section view of the frontal containment elements in FIG. 6A.

In addition, end and intermediary elements 40 and 50 are attached to the grille by the frontal securing elements 60, see FIG. 6A–C, introducing profiles 43 and 53 of each of the containment elements 40 and 50 in the channel 63 formed in the posterior part of such securing elements 60. In turn, frontal securing elements 60 are attached to grille 70, inserting rod 76 of grille 70 into channel 65 formed by the projection 67 of the securing elements 60.

Thus, each of the containment elements is maintained in its place on the grilles 70, both in their central and frontal parts, maintaining the possibility of sliding laterally, thus forming the entire structure of modular display shelves 11, 13, 15, 17 and 19.

Frontal securing elements 60 include, in addition, a channel 62 on their front face, which allows inserting a tape with legends or drawings, as well as a channel 66 on their upper face, which allows inserting a strip of acrylic or similar material 64, preventing the displayed products from falling when they are displaced towards the front.

Both ends of rods 72 and 74 of the grille 70 are inserted into perforations 84 and 82, respectively, of two brackets 80 (see FIGS. 8A and 8B) so that, when the projections 85, 87 and 88 of the brackets are inserted into grooves 95 or 97 of the stringers 94 of frame 90, all the shelves are secured to said frame 90 in a rotating manner.

Brackets 80 include an upper oval perforation 82 and a lower curve groove 84, which has an undercut 86 at its upper end. This configuration allows the entire displaced shelf to revolve downwards and upwards, from its display position to its replenishing position; when rod 74 of grille 70 falls into undercut 86, it allows the display shelf to remain in its horizontal position until it is lifted and taken out of the undercut, so that it returns by gravity to its display position.

In addition, bracket 80 includes two flanges 83, 89, which give stability to the entire display shelf after said bracket 80 has been joined to stringer 94 of frame 90, introducing the projections 85, 87, 88 in the grooves 95.

Stringers 94 of the frame 90 have two rows of grooves 95, 97, so as to be able to install, in modular fashion, one display next to another, inserting a bracket corresponding to a display shelf in the row of grooves 95, and introducing another groove corresponding to other adjacent display shelves in the row of grooves 97, thus obtaining the configuration of a modular display with variable length, adjusting the available display space for the products displayed at the point of sale.

The upper part of the frame, as well as its sides, are used to place decorative and advertising materials, as can be seen in FIG. 3, such as an awning 16, joined to the stringers 94 by attaching elements 18 and, on said awning, a support 14 for an advertising poster 12, as well as lateral covers 26 and 27, which can also hold containers 29, 31 for the advertising material of the products to be displayed.

The above description clearly shows that the same modular product display can contain products with different heights, by adding or removing display shelves, and products with different widths, by sliding and adding or removing intermediary containers, as well as interconnecting in a modular fashion two or more frames to increase display capacity, depending on the area available at the point of sale.

What is claimed is:

1. A modular display for consumer products comprising:
support frame including stringers;
at least two display shelves constructed and arranged to be rotated and displaced upwardly or downwardly with respect to said support frame, each of said display shelves including:
a support grille; and
a plurality of containment elements, including end containment elements and intermediary containment elements, arranged in lateral, side-by-side relation across said display shelf, each of said containment elements being laterally slidably connected to said support grille to permit relative sliding adjustment between adjacent pairs of said containment elements to thereby adjust the size of a product-receiving space therebetween, each of said end containment elements including a frontal wall, a lateral wall, a back wall, a bottom wall, and a guide element disposed on an upper part of said lateral wall, said guide element of said end containment element projecting transversely to one side of said lateral wall along at least a portion said lateral wall, and each of said intermediary containment elements including a frontal wall, a central wall, a back wall, a bottom wall, and a guide element disposed on an upper part of said central wall, said guide element of said intermediary containment element projecting transversely to opposite sides of said central wall along at least a portion of said central wall, wherein the guide element of each of said containment elements cooperates with the guide element of each laterally adjacent containment element to guide product sliding through the product-receiving space between the adjacent containment elements; and
bracket elements connected to opposite sides of each of said display shelves, each of said bracket elements being engageable with a selected portion of a corresponding one of said stringers to secure said display shelf at a selected position along said corresponding stringer, said bracket element being constructed and arranged to permit upward and downward rotation of said shelf with respect to said support frame and to permit locking of said shelf with respect to said support frame in either of a generally horizontal orientation or an inclined orientation.

2. The modular display of claim 1, wherein said guide elements of said end and intermediary containment elements project at substantially right angles to the respective lateral and central walls of said end and intermediary containment elements.

3. The modular display for consumer products according to claim 1, where an upper part and sides of the frame are adapted to hold covers or advertising and ornamental elements for the products to be displayed.

4. The modular display for consumer products according to claim 1, wherein said support grille includes a rod and where the end and intermediary containment elements for products are joined, with the ability of being released and slid, to said rod of the support grille by at least one U-shaped projection formed on the external side of the bottom wall of said containment elements.

5. The modular display of claim 1, wherein each of said stringers includes at least one row of longitudinal slots formed therein and said brackets are engageable with a portion of said slots of the corresponding one of said stringers to secure said display shelf at the selected position along said corresponding stringer.

6. The modular display for consumer products according to claim 5, where the stringers of the frame contain two parallel longitudinal rows of grooves, allowing for the adjacent placement of two product display shelves.

7. The modular display of claim 1, wherein each of said display shelves further includes a frontal securing element connected to a front edge of said support grille, and each of said containment elements is constructed and arranged to be laterally slidably connected to said support grille and to said frontal securing element.

8. The modular display for consumer products according to claim 7, wherein said support grille includes a front rod to which said frontal securing element is joined, and where at least one of the end and intermediary containment elements includes a profile formed on an external face of said front wall thereof, said profile being constructed and arranged to be engaged with said frontal securing element to slidably secure said containment element to said frontal securing element.

9. The modular display for consumer products according to claim 8, where the frontal securing elements include a groove on their rear side, suitable to be adjusted to the shape and size of the profile of the containment elements, and a projection in its lower part which joins them, with the possibility of releasing them, to the front rod of the support grille.

10. The modular display for consumer products according to claim 9, where the frontal securing elements also include a groove on their front side, which allows for the insertion of an acrylic slip, which prevents the displayed products from falling when they are displaced towards the front of the display.

11. The modular display for consumer products according to claim 9, where the frontal securing elements also contain a groove on their front side, which allows for the insertion of a strip with legends or drawings.

12. The modular display for consumer products according to claim 1, where the bracket elements contain an oval groove on their top part, and a semicircular groove in their lower part, so that two back rods of the support grille are introduced into respective ones of said oval and semicircular grooves, in order to allow the display shelves to rotate.

13. The modular display for consumer products according to claim 12, where the semicircular groove also contains an undercut at its top, allowing the back rod of the support grille to enter into said slot, when the display shelves rise to their horizontal position, maintaining the display shelf in a horizontal position.

14. The modular display of claim 12, wherein the two back rods are fixed to said display shelf at a fixed distance from one another.

15. The modular display for consumer products according to claim 12, where bracket elements contain two projections at the back end of their lateral sides, diametrically opposed, which give stability to the product display shelves.

16. The modular display for consumer products according to claim 12, where the bracket elements also contain at least one L-shaped securing element, on its back side, suitable to join the bracket to the frame.

17. The modular display of claim 16, wherein said at least one L-shaped securing element comprises three L-shaped securing elements.

\* \* \* \* \*